United States Patent [19]
Lipson et al.

[11] Patent Number: 6,099,524
[45] Date of Patent: *Aug. 8, 2000

[54] ELECTROPHYSIOLOGICAL MAPPING AND ABLATION CATHETER AND METHOD

[75] Inventors: David Lipson, Poway; Marc Jensen, San Marcos, both of Calif.

[73] Assignee: Cardiac Pacemakers, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/188,187

[22] Filed: Jan. 28, 1994

[51] Int. Cl.$^7$ ............................... A61B 17/39; A61N 1/05
[52] U.S. Cl. ........................... 606/41; 600/374; 600/509; 607/122
[58] Field of Search ................................. 606/27, 28, 29, 606/31, 39, 40, 41, 45, 48, 49, 50; 607/96, 98, 115, 116, 119, 122; 600/373, 374, 509

[56] References Cited

U.S. PATENT DOCUMENTS

| | | | |
|---|---|---|---|
| Re. 33,925 | 5/1992 | Bales et al. | 606/48 |
| 4,449,528 | 5/1984 | Auth et al. | |
| 4,492,231 | 1/1985 | Auth | |
| 4,492,731 | 1/1985 | Bankar et al. | 428/362 |
| 4,945,912 | 8/1990 | Langberg | 128/642 |
| 5,005,587 | 4/1991 | Scott | 607/122 |
| 5,122,137 | 6/1992 | Lennox | 606/40 |
| 5,156,151 | 10/1992 | Imran | 128/642 |
| 5,190,539 | 3/1993 | Fletcher et al. | 606/25 |
| 5,230,328 | 7/1993 | Buchholtz et al. | 128/24 |
| 5,230,349 | 7/1993 | Langberg | 128/786 |
| 5,231,248 | 7/1993 | Shah | 174/76 |
| 5,257,635 | 11/1993 | Langberg | 607/122 |
| 5,423,811 | 6/1995 | Imran et al. | 606/41 |
| 5,500,012 | 3/1996 | Brucker et al. | 607/122 |
| 5,606,974 | 3/1997 | Castellano et al. | 600/438 |
| 5,735,280 | 4/1998 | Sherman et al. | 128/600.03 |
| 5,755,760 | 5/1998 | Maguire et al. | 607/122 |

FOREIGN PATENT DOCUMENTS

| | | | |
|---|---|---|---|
| WO 92/02272 | 2/1992 | WIPO | A61N 1/05 |
| WO 93/08755 | 5/1993 | WIPO | A61B 17/36 |
| WO 93/15652 | 8/1993 | WIPO | A61B 5/02 |
| WO 93/20769 | 10/1993 | WIPO | A61B 17/36 |

OTHER PUBLICATIONS

In Vitro Evaluation Of The Antimicrobial Efficay And Biocompatibility Of Silver–Coated Central Venous Catheter; B. Jansen et al.; Institute of Medical Microbiology and Hygiene, University of Cologne, Germany; J. Biomater Appl. (United States) Jul. 1994, 9(1) pp. 55–70.

New Processes For Surface Treatment Of Catheters; P. Siopshansi; Spire Corporation, Beford, Massachusetts 01730–2396; Artif Organs (United States) Apr. 1994, 18(4) pp. 266–271.

The Biocompatibility Of Silver; D. F. Williams; First International Conference on Gold and Silver in Medicine; The Gold Institute and the Silver Institute; 1987 pp. 262–272.

(List continued on next page.)

*Primary Examiner*—Jennifer Bahr
*Assistant Examiner*—Sonya Harris-Ogugua
*Attorney, Agent, or Firm*—Fulwider, Patton Lee & Utecht, LLP

[57] ABSTRACT

A mapping and ablating catheter having a short distal tip electrode comprising a bio-compatible outer surface and a thermal dissipating mass for dissipating heat received by the electrode. The outer surface may be formed by plating a thin layer of gold or platinum on the dissipating mass, or the entire electrode may be formed of a homogenous material such as a gold alloy that is bio-compatible thereby forming the outer surface with the mass itself. An alloy having a thermal conductivity greater than pure platinum is used so that the ablation procedure can be completed before exceeding the temperature limits. In one case, the entire electrode was formed of a 88% gold 12% nickel alloy. The electrical feed to the electrode is oversized to also dissipate heat received by the electrode. The electrode is no greater than five mm in length yet produces an ablation volume equal to or greater than longer electrodes. One or more band electrodes may also include thermal dissipating masses.

32 Claims, 4 Drawing Sheets

OTHER PUBLICATIONS

The Biocompatibility Of Silver; William R.L., P.J. Doherty et al.; Crit Rev. Biocompat. vol. 5, No. 3, 1989, pp. 221–244.

Leonard T. Blouin, Frank I. Marcus, and Louis Lampe, "Assessment of Effects of a Radiofrequency Energy Field and Thermistor Location in an Electrode Catheter on the Accuracy of Temperature Measurement," *PACE*, May 1991, pp. 807–813.

Michael Oeff, Jonathan J. Langberg, Michael Chin, Walter E. Finkbeiner, and Melvin Scheinman, "Ablation of Ventricular Tachycardia Using Multiple Sequential Transcatheter Application of Radiofrequency Energy,"*PACE*, Aug. 1992, pp. 1167–1176.

Karl–Heinz Kuck and Michael Schluter, "Radiofrequency Catheter Ablation of Accessory Pathways," *PACE*, Sep. 1992, pp. 1380–1386.

Leonard T. Blouis and Frank I Marcus, "The Effect of Electrode Design on the Efficiency of Delivery of Radiofrequency Energy to Cardiac Tissue In Vitro," *PACE*, Jan. 1989, pp. 136–143.

Jonathan J. Langberg, Marsha Gallagher, S. Adam Strickberger, and Omar Amirana, "Temperature–Guided Radiofrequency Catheter Ablation With Very Large Distal Electrodes," *Circulation*, Jul. 1993, pp. 245–249.

Leonard T. Blouin, Frank I. Marcus, and Louis Lampe, "Assessment of Effects of a Radio–frequency Energy Field and Thermistor Location in an Electrode Catheter on the Accuracy of Temperature Measurement" PACE, May 1991, pp 807–813.

ELECTROPHYSIOLOGICAL MAPPING AND ABLATION CATHETER AND METHOD

BACKGROUND

The invention relates generally to mapping and ablating tissue, and more particularly, to an improved system and method for mapping and ablating cardiac tissue with the same electrode.

In many cases, damaged tissue interferes with the proper functioning of an organism. As one example, the sinus and AV nodes provide the electrical control signals that cause the correct movement of the heart in pumping the blood to the body. Damage to tissue between such nodes may cause the control signals to be disrupted resulting in cardiac arrhythmias.

While there are different treatments for cardiac arrhythmias, including the application of anti-arrhythmia drugs, ablation of such damaged tissue has been found in many cases to restore the correct operation of the heart. Such ablation may be performed during open heart surgery; however, a preferred therapeutic procedure is percutaneous ablation. In this procedure, a catheter is percutaneously introduced into the patient and directed through an artery to the atrium or ventricle of the heart to perform single or multiple diagnostic, therapeutic, and/or surgical procedures. These catheter devices typically include five or six lumina used for different purposes such as carrying electrical wires, body fluids, or drugs.

A steerable electrophysiological ("EP") catheter may be used to position an electrode or electrodes for systematically scanning selected endocardial sites within the heart to detect the propagation of wave electrical impulses as they propagate across the heart during each contraction. Through the detection of irregular electrical impulses, the locations of damaged cells may be revealed. Once these damaged cells have been located, the physician may use an ablation procedure to destroy the damaged cells in an attempt to remove the depolarization wave obstruction and restore normal heart beat. Characteristics required of a percutaneous EP catheter include small size and flexibility.

Before the damaged tissue can be ablated, it must be located with some precision so that the ablation energy can be accurately directed. Ablation of undamaged tissue is undesirable as is only partial ablation of the damaged tissue. Numerous types of EP catheters have been developed for more accurately locating the damaged tissue. As indicated above, selected endocardial sites may be successively scanned or mapped to locate damaged tissue. A desirable characteristic of the mapping device is small size. The smaller the size, the higher the resolution that can be obtained in identifying damaged tissue. Larger scanning electrodes contact more surface area and therefore have lower resolution. Mapping electrodes of one millimeter in length have been disclosed.

Another characteristic desired of an EP catheter is the ability to perform both the mapping procedure and an ablation procedure without having to withdraw the catheter and re-introduce it or a different one into the patient. It is undesirable to have to replace a mapping catheter with a separate ablation catheter because of the increased trauma caused the patient and the difficulty of locating the replacement catheter exactly in the position of the replaced catheter. Thus, EP catheters have been developed that are capable of performing both mapping and ablation procedures without removing them from the patient once positioned.

A typical EP catheter includes an electrical connector at its proximal extremity that is coupled to the appropriate equipment to conduct the mapping and ablation procedures. For example, during mapping the electrical lines connected to the catheter electrodes will be connected through the connector to analysis equipment comprising computer controlled electrical signal sensors. During the ablation procedure, the electrical line or lines connected to one or more of the catheter electrodes, preferably the distal tip electrode, will be connected through the connector to a power box for supplying up to 100 watts of power at a frequency between 100 kHz to 30 mHz with variable or fixed impedance.

A typical EP catheter is shown in FIG. 1 and is described in further detail below. The catheter 10 includes an active electrode 12 at the distal tip 14 of the catheter tube 20 and ring electrodes 16 around the diameter of the tube spaced proximally from the distal electrode 12. The electrodes are connected to the proximal end of the catheter 18 with thin, flexible wires.

After the endocardium has been mapped and damaged tissue identified, ablation of the damaged tissue can be performed. Many EP catheters use radio frequency (RF) technology to destroy the damaged endocardial cells. The use of radio frequency energy for cardiac ablation has gained widespread acceptance and success in treating arrhythmias. Thermal tissue damage and ablation occur as a result of the application of radio frequency energy to cardiac tissue.

In practice, the catheter distal tip 14 is fitted with an electrode 12 used both for mapping and for emitting RF energy to destroy the target damaged cells. Such an active electrode is the source of an electrical or electromagnetic field that causes heating of the contacting and neighboring tissue. To be most effective, the electrode at the distal end of an RF ablation catheter is placed in intimate contact with the target endocardial tissue in order to avoid leaving a gap in which concentrated energy might boil the blood in the intracardial volume. However, even though the electrode is pressed into intimate contact with the endocardium, typically a portion of the electrode will be in contact with the blood. This is true in both the unipolar and bipolar approaches.

In the approach commonly referred to as "unipolar," a large surface area electrode is placed on the chest of the patient to serve as a return for completing the electrical ablation circuit with one of the catheter electrodes. In a bipolar approach, typically two electrodes on the catheter are used to complete the electrical circuit. This circuit may include the tip electrode and a band electrode located proximal to the tip. In the bipolar approach, the flux traveling between the two electrodes of the catheter enters the endocardium to cause ablation. In the bipolar system, as in the unipolar system, portions of the active electrodes typically are in contact with the blood so that boiling can occur if those electrodes reach an excessive temperature.

The temperature boundary between viable and non-viable tissue is approximately 48° Centigrade. Tissue heated to a temperature above 48° C. becomes non-viable and defines the ablation volume. For therapeutic effectiveness, the ablation volume must extend a few millimeters into the endocardium and must have a surface cross-section of at least a few millimeters square. The objective is to elevate the tissue temperature, generally at 37° C., fairly uniformly to the ablation temperature above 48° C., keeping the hottest tissue temperature below 100° C. At approximately 100° C. charring and boiling of the blood take place. Charring is particularly troublesome at the surface of the catheter electrode because the catheter must be removed and cleaned before the procedure can continue. Additionally, charring and boiling of the blood seriously modify the electrical conductivity of blood and tissue and cause an increase in the overall electrical impedance of the electrical heating circuit and a drop in the power delivery to the tissue. Too great a rise in impedance can result in sparking and thrombus formation within the heart, both of which are undesirable.

Even though no significant amount of heat is generated in the RF energy electrode itself, adjacent heated endocardial tissue heats the electrode via heat conduction through the tissue. As mentioned above, part of the active electrode will be in contact with the blood in the heart and if the electrode temperature exceeds 90–100°, it can result in blood boiling and clotting on the electrode. The application of RF energy must then be stopped. However, shutting the RF generator off due to the temperature rise may not allow sufficient time to complete the entire ablation procedure. Providing an ablation electrode capable of applying higher amounts of power for a longer period of time to ablate the damaged tissue to an acceptable depth is a goal of current ablation catheter electrode design. It has been found that higher power for longer time periods results in a higher probability of success of the ablation procedure.

Numerous studies have been performed on means to obtain greater ablation depths with an ablation electrode. For example, see Langberg, Lee, Chin, Rosenqvist, *Radiofrequency Catheter Ablation: The Effect Of Electrode Size On Lesion Volume In Vivo*, PACE, Oct. 1990, pages 1242–1248; Kuck and Schlüter, *Radiofrequency Catheter Ablation of Accessory Pathways*, PACE, Vol. 15, Sep. 1992, pages 1380–1386; and Langberg, Gallagher, Strickberger, Amirana, *Temperature-Guided Radiofrequency Catheter Ablation With Very Large Distal Electrodes*, Circulation, Vol. 88, No. 1, July 1993, pgs 245–249. In each of these cases, the conclusion appears to favor a larger electrode; for example 8 mm in length. As a result, many EP catheter manufacturers have increased the size of the ablation electrode to obtain an increased ablation depth referred to in these papers. However, larger size electrodes are more difficult to steer into and position in the cardiac site and additionally, are not as desirable for mapping purposes. The electrode selected for ablation is usually mounted on the distal tip of the catheter and that location is excellent for mapping procedures. Increasing the size of that electrode not only makes it more difficult to steer into the mapping and ablation sites, but also provides lowered resolution in the mapping procedure as pointed out above. A larger electrode results in less sensitivity or resolution to determine the exact location of the aberrant tissue. It is thought by many skilled in the art that an eight mm length results in an electrode unsuitable for mapping purposes due to this lack of resolution.

However, reducing the size of the electrode is discussed in these references as resulting in a lower power handling capability with less desirable ablation patterns. For example, the Kuck and Schlüter paper points out that the ablation success rate was significantly increased by use of a 4 mm length tip electrode over a 2 mm length electrode (page 1383, right column). Since that publication date of Kuck and Schlüter, the Langberg papers discuss that 8 mm tips provide improved results. The inventors believe that these publications are representative of the current state of the art in which larger electrode lengths are used for ablation regardless of their degraded mapping performance.

The inventors believe that most, if not all, ablation electrodes currently in use are constructed of pure platinum or a platinum iridium alloy, typically "platinum 10 iridium" (90% platinum 10% iridium). Platinum has a relatively low thermal conductivity of approximately or less than:

$$0.165 \frac{cal \times cm}{s \times °C. \times cm^2}$$

where cal=calories, cm=centimeters, s=seconds, and C=Centigrade (ASM Metals Handbook Desk Ed., pgs. 1–52, 1985). While the platinum or platinum 10 iridium alloy is desirable because of it bio-compatibility, its low thermal conductivity decreases its ability to dissipate heat. Consequently, if the electrode is too small, it will provide poor dissipation of the heat accumulating in itself from its contact with the heated tissue. This poor heat dissipation may not be rapid enough and early termination of the ablation procedure would be required to avoid blood boiling and coagulation. If the ablation procedure is terminated too early, it will not be complete, the ablation procedure may not be successful, and must be repeated.

To avoid this undesirable situation, manufacturers are making platinum 10 iridium ablation electrodes larger so there will be greater surface area of the electrode in contact with the tissue to be ablated, larger amounts of power can be applied, and ablation will take a shorter time. Additionally, the larger size of the electrode will assist in heat dissipation. Disadvantages of larger electrodes as discussed above include lowered accuracy as a mapping electrode, less localization of the ablation energy, and difficulty in introducing and positioning the electrode in a patient. Not only do smaller electrodes map better, they also better focus the RF energy to the damaged tissue site thereby limiting ablation of undamaged tissue.

Some manufacturers provide electrodes that are smaller in size than the above-discussed ablation electrodes and are formed out of pure platinum, which has a higher thermal conductivity than platinum 10% iridium. However, to the inventors' knowledge, these electrodes are specified by the manufacturer for mapping purposes, not ablation. While pure platinum has a higher thermal conductivity than platinum 10 iridium, it is still relatively low when compared to other materials and heat build up in an electrode formed of pure platinum when used for ablation is still of substantial concern.

Another concern related to EP catheters is the ability to monitor the ablation electrode temperature. Knowing when that temperature is approaching and then finally reaching 90–100° can greatly assist a physician in successful control over the procedure. However, the thermal conductivity of the materials surrounding the temperature sensor can affect its accuracy, especially in the case where the sensor is located internally in the ablation electrode.

It has been noted in some cases where the ablation electrode is formed of platinum 10 iridium and the sensor is located internal to the electrode as opposed to being mounted on the outer surface of the electrode, that the temperature at the outer surface of the electrode can be higher than the temperature at the sensor due to the slower thermal conduction of the material. There is thus a time lag and hence, the temperature indicated by the temperature sensor signal is suspect.

Hence, those skilled in the art have recognized the need for an electrode small enough to provide increased resolution when used for mapping purposes, yet large enough to perform a complete ablation procedure without exceeding temperature limits. Additionally, the electrode has to be formed of a bio-compatible material for the internal use with a patient. Furthermore, those skilled in the art have recognized the need to provide an ablation electrode small enough for increased maneuverability in the patient, that requires less ablation energy to ablate the target tissue, and that localizes the ablation energy to avoid ablating undamaged tissue. Additionally, an electrode design that enhances the ability to obtain more accurate temperature sensor signals is desirable. The present invention fulfills these needs and others.

SUMMARY OF THE INVENTION

Briefly and in general terms, the invention is directed to a catheter and a method for mapping and ablating biological tissue, the biological tissue being located in a biological structure in which fluids flow past the tissue to be ablated. The catheter has a size such that it can be percutaneously introduced and positioned at the tissue to be mapped and ablated. Additionally, the catheter comprises an electrode mounted at the distal end of the catheter body member, the electrode having a size suitable for accurate and relatively high resolution mapping and a shape and length such that when positioned against the tissue to be ablated, a portion of the electrode will be exposed to the fluids in the biological structure for communicating heat to those fluids thereby cooling the electrode.

The electrode comprises an outer surface and a thermal dissipating mass for rapidly conducting heat received by the electrode to the fluids surrounding the electrode. The outer surface is formed of a biologically compatible material and the thermal dissipating mass has a thermal conductivity exceeding that of pure platinum and of platinum 10 iridium.

In a more detailed aspect in accordance with the invention, the outer surface of the electrode is formed by intimately bonding an outer layer of bio-compatible material to the thermal dissipation mass. The outer layer of material is formed of a pure substance or an alloyed substance for contact with the tissue to be ablated while the thermal dissipation mass is formed of a material having a high thermal conductivity. The outer layer is relatively thin so that its effect on the overall thermal conductivity of the electrode will be relatively small. Its purpose is to provide an electrically conductive and bio-compatible outer surface. The material selected for the thermal dissipation mass can therefore be selected more on its thermal conductivity than on its bio-compatibility. For example, silver or copper or an alloy of each coated with a gold or platinum outer layer may be considered. The material chosen for the thermal dissipation mass has a thermal conductivity greater than pure platinum.

In yet a further detailed aspect in accordance with the invention, the outer surface of the electrode is selected from the group of bio-compatible materials consisting of gold and its alloys, e.g., 14 karat gold, platinum, titanium, tungsten, stainless steel, and cobalt based bio-compatible materials.

In another aspect, the electrode is formed entirely of a homogenous bio-compatible material having a thermal conductivity exceeding pure platinum. In a more detailed aspect, the homogenous material is selected from the group of bio-compatible materials consisting of gold alloy; pure titanium, and pure tungsten. The homogenous electrode therefore provides both the bio-compatible surface and the thermal dissipation mass.

In a more detailed aspect, the catheter further comprises an electrical conductor connected to the electrode and extending to the proximal end of the body member of the catheter, the electrical conductor being formed of a material having a thermal conductivity at least as great as copper or copper alloys such as copper alloyed for tensile strength, and having a larger diametrical size than the size needed to conduct the amount of electricity to the electrode for ablation. Because of its increased size, the electrical conductor forms a part of the thermal dissipating mass and conducts heat away from the electrode.

In further aspects, the electrode has a generally cylindrical shape with a rounded end and the length of the electrode is no greater than five millimeters.

In the method in accordance with the invention, biological tissue located in a biological structure in which fluids flow past the tissue is mapped and ablated. The method comprises the steps of forming an electrode of a biologically compatible material having a size suitable for accurate and relatively high resolution mapping, a thermal conductivity exceeding that of pure platinum, and having a thermal dissipating mass, mounting the electrode at the distal end of a percutaneous catheter, percutaneously positioning the electrode so that it makes contact with the tissue to be mapped, positioning the electrode so that it makes contact with the tissue to be ablated such that a substantial portion of the electrode is positioned for contact with the fluids in the biological structure, applying ablation energy to the electrode to cause heating of the tissue to be ablated to a level where the tissue is non-viable, and conducting heat from the electrode to the fluids in the chamber thereby cooling the electrode during the ablation process.

In a more detailed aspect of the method in accordance with the invention, the step of forming an electrode comprises the steps of intimately bonding an outer layer of bio-compatible material to the thermal dissipation mass where the outer layer is relatively thin so that its effect on the overall thermal conductivity of the electrode will be relatively small.

Yet a further detailed method step relating to the step of intimately bonding the outer surface to the inner core comprises plating the outer surface to the thermal dissipating mass and forming the thermal dissipating mass of a material having a thermal conductivity exceeding pure platinum.

In the step of forming an electrode, a more detailed aspect comprises the step of selecting the material for the outer surface from the group of bio-compatible materials consisting of gold and its alloys, e.g., 14 karat gold, platinum, titanium, tungsten, stainless steel, and cobalt based bio-compatible materials.

In yet a further detailed method aspect, the step of forming an electrode comprises the step of forming the electrode entirely of a homogenous bio-compatible material having a thermal conductivity exceeding pure platinum. In a more detailed aspect, the homogenous material is selected from the group of bio-compatible materials consisting of gold alloy; pure titanium, and pure tungsten.

A further detailed aspect comprises forming an electrical conductor of a material having a thermal conductivity at least as great as a copper alloy, and having a larger diametrical size than the size needed to conduct the amount of electricity to the electrode for ablation, connecting the electrical conductor to the electrode and extending the conductor to the proximal end of the percutaneous catheter, and conducting away heat received by the electrode with the electrical conductor.

In a further detailed aspect, the step of forming an electrode comprises the step of forming the electrode with a generally cylindrical and having a rounded end and having a length no greater than five mm.

In yet a further aspect, one or more band electrodes includes a bio-compatible outer surface and a thermal dissipation mass. A temperature sensor may also be included in such band electrode. The thermal dissipation mass of the band electrode is formed of a material having a thermal conductivity exceeding pure platinum.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
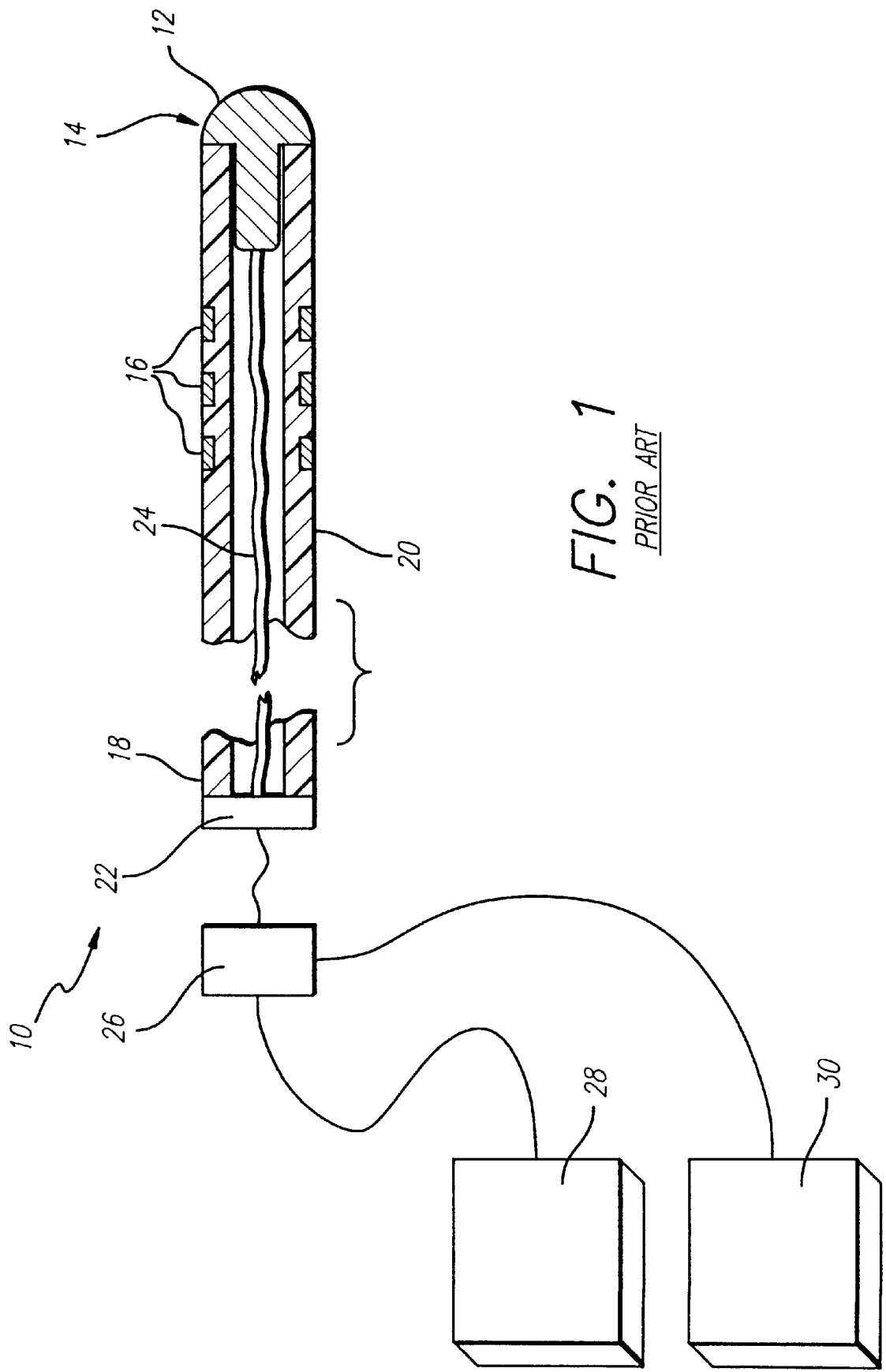
FIG. 1 is a block diagram of a prior art EP catheter connected to analysis and power equipment showing the connection to an active tip electrode formed of platinum 10 iridium.

In the following description, like reference numerals will be used to refer to like or corresponding elements in the different figures of the drawings. Referring now to the drawings and particularly to FIG. 1, there is shown a typical electrical catheter 10 with an active distal tip electrode 12. The active electrode 12 is used for mapping and for applying ablation energy to selected cardiac tissue. A plastic catheter tube 20 connects the distal tip active electrode 12 to a connector 22 at the proximal end 18. An electrical wire 24 electrically connects the active electrode 12 to the connector 22. Ring electrodes 16 are also mounted to the catheter tube 20 for mapping purposes. Although not shown, flexible electrical wires are also connected between the ring electrodes and the connector 22.

The connector 22 is used to provide electrical connections between the electrode wires and the appropriate external equipment for mapping and ablation procedures. For example, in FIG. 1, a switching device 26 selectively connects the electrodes between a mapping analyzer 28 and a power device 30, such as an RF power supply for generating RF energy to be conducted to the active electrode 12 for ablation of target tissue. To maintain flexibility, the connecting wire 24 is relatively thin with a typical size of twenty-eight gauge copper wire with a 0.4 millimeter (mm) diameter.

The connection of the catheter to the electrical power source 30 can be between two electrodes on the catheter (bipolar arrangement) or between one catheter electrode and a large neutral external skin electrode (unipolar arrangement—not shown). A unipolar power supply connection is discussed herein and shown in FIG. 1. Mapping analyzers 28, RF energy sources 30, and switching devices 26 are well known to those skilled in the art and no further details are presented here.

The objective of the thermal design of the electrode of FIG. 1 is to heat a controlled volume of tissue to an ablation temperature while at the same time assuring that the peak temperature is away from the electrode surface 12 so that charring does not foul the active electrode surface and blood boiling does not occur. The distal end of the active electrode 12 provides a bare metal interface to the tissue and generates a heating pattern in the tissue due to the transmission of RF power into the tissue. In operation, power is typically increased in order to increase the ablation volume until an impedance change is noticed due to the onset of charring or the temperature limit of the electrode is exceeded. However as discussed above, the thermal conductivity of the materials used in the electrode 12 can affect the time that ablation energy can be applied to the tissue as well as the accuracy of any temperature sensor mounted in the electrode.

Figure 2:
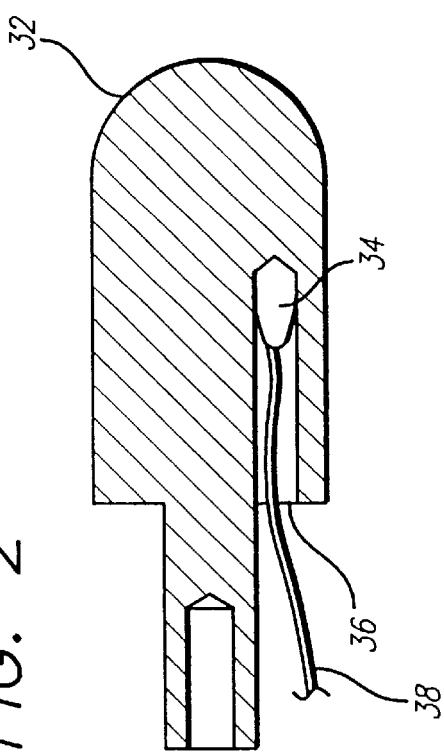
FIGS. 2 and 3 present cross-section and end views respectively of details of temperature sensor mounting in an ablation electrode.
Figure 3:
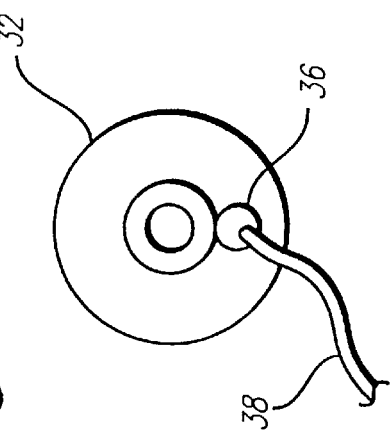

In FIGS. 2 and 3 there is shown a catheter distal tip electrode 32 having a temperature sensor 34 mounted internally in the electrode. A chamber 36 has been bored into the electrode to contain the sensor 34. The sensor 34 may take different forms, two of which are a thermistor or a thermocouple. Different techniques for mounting the sensor are known to those skilled in the art and no further details are presented here. The sensor wire 38 is connected to the appropriate monitoring equipment as is well known to monitor electrode temperature.

Figure 4:
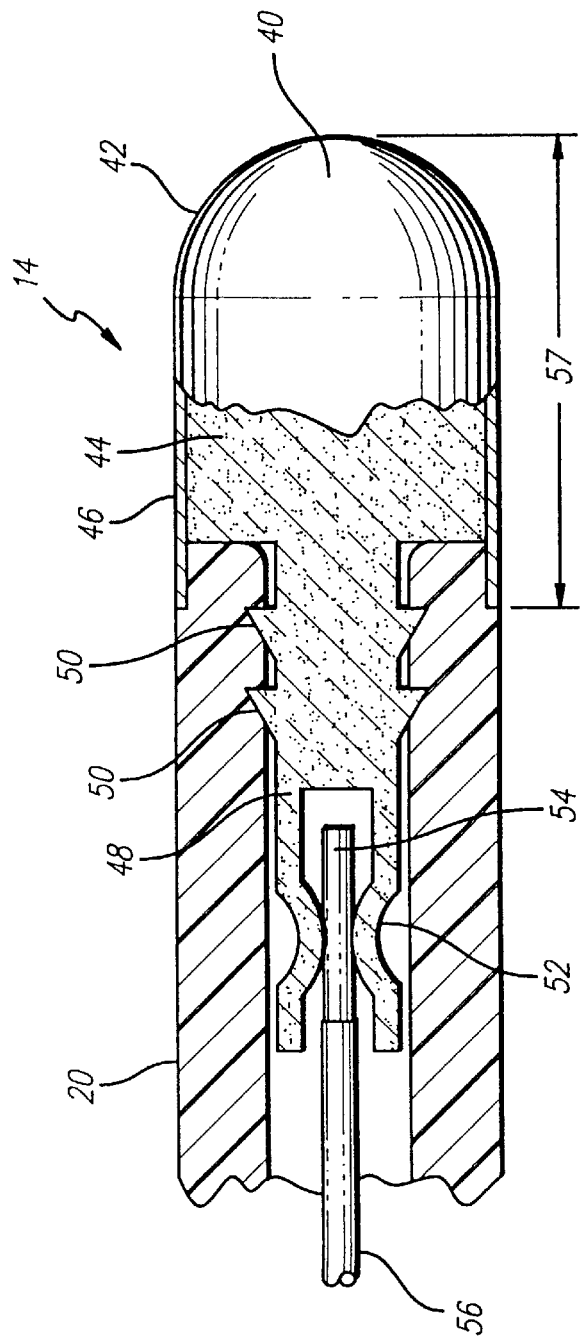
FIG. 4 presents a first embodiment of the distal end of a mapping and ablation catheter in accordance with the principles of the invention showing an electrode usable for both mapping and ablation and having an outer layer of bio-compatible material over a thermal dissipating mass.

Referring now to FIG. 4, an electrode design incorporating principles of the invention is shown. The distal end of the catheter 14 includes a distal tip electrode 40 having an outer surface 42 and a thermal dissipation mass 44. In the embodiment shown, the outer surface 42 comprises a cap or layer 46 that covers the thermal dissipating mass 44 and extends over a part of the catheter tube 20, in this case approximately 0.25 mm. For mounting purposes, the thermal dissipating mass 44 includes a stem 48 having annular mounting rings 50 shaped as barbs. The stem 48 with its rings 50 is pressed into the distal end of the catheter tube 20 and because of the shape of the barb rings, the tip electrode 40 remains in place with a large pull-out force required for disassembly. The stem also includes a crimping device 52 for receiving the conductor 54 of the electrical wire 56 connecting the tip electrode 40 to a main connector located at the proximal end of the catheter (not shown) similar to the arrangement shown in FIG. 1. The crimp device 52 forms an intimate electrical and thermal contact with the wire conductor 54 as will be discussed in more detail below.

To avoid possible injury to the patient, both the outer surface of the tube 20 and the outer layer 46 of the tip electrode 40 are formed of bio-compatible materials. They are chemically inert or passivated and are bio-compatible. For example, the outer surface of the tip electrode 40 is formed of a gold alloy. Because the thermal dissipating mass 44 is not exposed to the patient, it may be formed of a material not necessarily bio-compatible but having a high thermal conductivity. For example, the thermal dissipating mass 44 may be formed of copper or silver. The outer layer 46 would then be intimately bonded to the thermal dissipating mass 44 by means well known to those skilled in the art. For example, the layer 46 can be held in place by thermally conductive epoxy, by brazing, swaging, crimping, press forming or other means.

While gold is desirable as the outer layer 46 due to its bio-compatibility and its relatively high thermal conductivity, it may be alloyed to increase its hardness and to ease machining into the proper shape. Although the inventors have found that in many cases alloying a relatively high thermal conductivity metal with another for strength causes the thermal conductivity to decrease dramatically, such an effect has been offset somewhat by making the volume of the outer layer 46 very small in comparison to the volume of the thermal dissipating mass 44. Thus the decrease in thermal conductivity caused by alloying the outer layer gold with 12% nickel will be relatively small when compared to the electrode 40 volume as a whole. For example, in the case of a seven French tip electrode that is four mm long with a machined or stamped cap 46 bonded to the thermal dissipating mass 44 (FIG. 3), the cap was 0.08 mm (0.003 in) thick and made up only fourteen percent (14%) of the entire volume of the electrode. The outer layer may be formed by means such as separately manufacturing a cap and bonding it to the thermal mass 44, plating, vapor deposition, or electro-depositing gold or gold alloy over a silver or copper thermal dissipation mass. And when deposition is used, the volume of the outer layer as compared to the volume of the electrode as a whole may even be smaller than the above example. Techniques for plating and electro-deposition of gold on other substances are well known to those skilled in the art and are not discussed in further detail here.

Also forming a part of the thermal dissipation mass is the stem 48 used to mount the electrode 40 firmly into the catheter tube 20. It likewise is formed of a material having a high thermal conductivity and will dissipate heat received by the electrode 40. In this case, the stem is integral with the thermal dissipation mass 44, although other arrangements are possible. As a further means of dissipating heat, the electrical conductor 54 used to electrically connect the ablation electrode 40 to the proximal catheter connector is a larger size than that needed to conduct just the electrical power for ablation. It is made of copper or a copper alloy having a relatively high thermal conductivity and is therefore available to dissipate heat. As is well known, copper may be alloyed to increase its tensile strength. Copper beryllium is one common example also usable here.

During the ablation process, the distal electrode 40 will be positioned in contact with the cardiac tissue to be ablated. Because of its generally cylindrical shape with a rounded distal end, a substantial surface area of the electrode will be available to make contact with the blood flowing past the electrode in the heart. The electrode 40 is designed to have a high thermal conductivity and much of the heat received by the electrode from the heated tissue will be rapidly conducted through the electrode along to the flowing blood thereby assisting in cooling the electrode. Additionally, heat will be conducted through the stem 48 and electrical conductor 54 for dissipation.

Because of the electrode's efficient thermal dissipation characteristics, it can handle a greater amount of power resulting in a larger ablation volume. Additionally, this efficiency in heat dissipation permits the electrode to be made smaller than prior electrodes. In one embodiment, a six French size electrode formed of 88% gold, 12% nickel having a length of two mm achieved an ablation volume twice as large as the ablation volume created by a six French, two mm length electrode formed of pure platinum. As used herein, the length of the electrode refers to the portion distal to the distal end of the catheter body 20. The length of the electrode is commonly determined by the length of exposed electrode surface and in FIG. 4, is indicated by numeral 57. Because of the efficiency of heat dissipation provided by the electrode shown in FIG. 4, such electrodes having five mm in length or less may be used for ablation.

Figure 5:
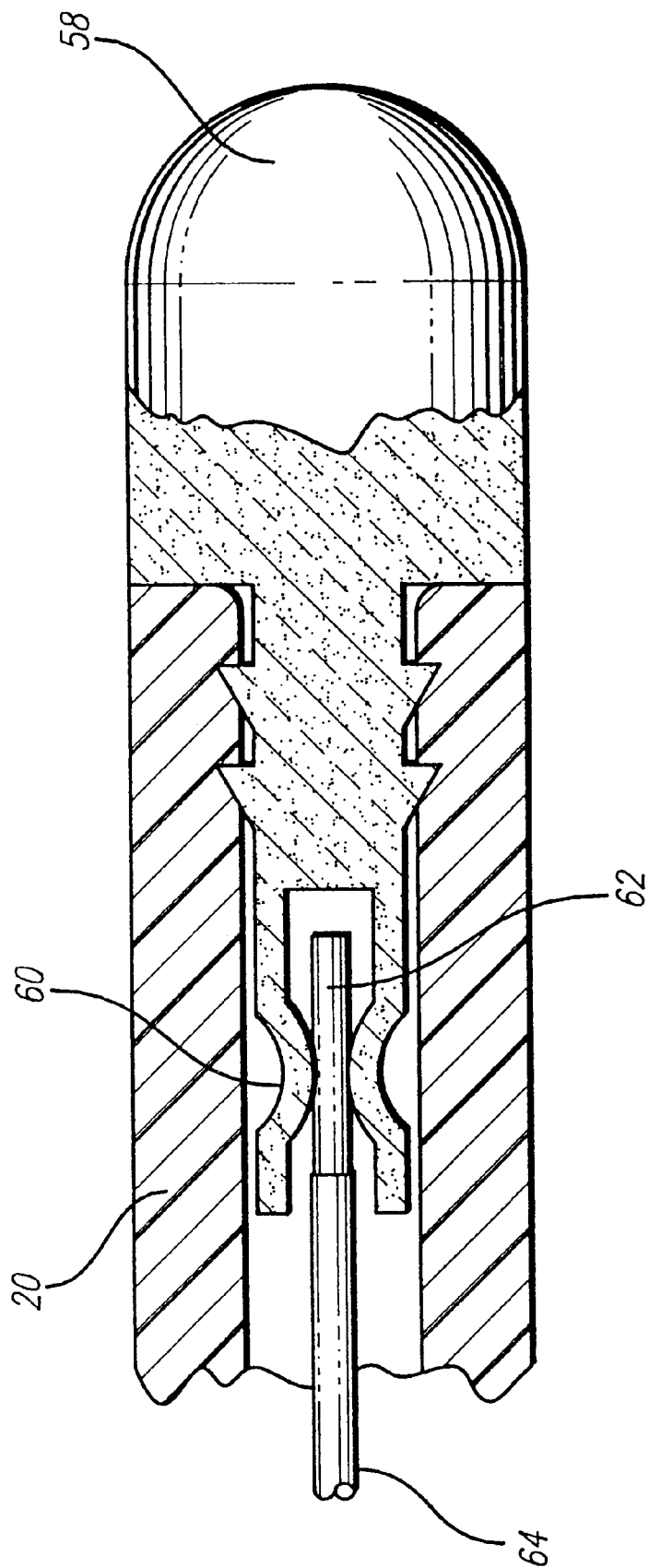
FIG. 5 presents an electrode formed entirely of a bio-compatible material, the material forming both the bio-compatible surface and the thermal dissipating mass.

Referring now to FIG. 5, a second embodiment of an electrode 58 in accordance with the principles of the invention is shown. In this case, the entire electrode 58 is formed of a homogenous alloy having a thermal conductivity exceeding pure platinum and platinum 10 iridium. The alloy must be bio-compatible because no outer protective layer exists. In one embodiment, the electrode was formed entirely of an 88% gold 12% nickel alloy which achieves a higher thermal conductivity than pure platinum and approximately four times greater thermal conductivity than platinum 10 iridium even though its thermal conductivity is only approximately one-half that of pure gold. While alloying a material can dramatically reduce its thermal conductivity, nevertheless, alloying may be required many times for improving structural strength. For example, machining pure gold accurately and repeatably can be difficult due to its softness. Alloying gold with nickel greatly improves its hardness while still resulting in a high thermal conductivity. As pointed out, its thermal conductivity is greater than pure platinum. While alloying gold is preferred, it is not required and a solid gold electrode may be used instead. It has been found that a 12% alloy with nickel only lowers the thermal conductivity of the gold by approximately 50%. While lowered thermal conductivity is undesirable, its increased producibility offsets the loss. On the other hand, prior electrodes formed of platinum 10 iridium experienced a loss of approximately 50% to 60% of thermal conductivity when compared to pure platinum.

The thermal conductivity of gold/nickel alloy is greater than pure platinum and the gold alloy of the electrode 58 will act also as the thermal dissipating mass in addition to providing the bio-compatible outer surface. As in the previous embodiment, a crimping device 60 and enlarged conductor electrical 62 of a wire 64 are used to increase thermal dissipation. The embodiment of FIG. 5 also permits the use of a two mm electrode to obtain a substantial ablation volume. As in FIG. 4, the efficiency in heat dissipation provided by the electrode shown in FIG. 5 permits electrodes of five mm or less in length to be used for ablation.

While gold has been discussed above as the preferred material for the electrode, or in the first embodiment, the outer layer, other materials may also function acceptability. It has been found that materials having a thermal conductivity exceeding pure platinum can also function acceptably.

The use of a high thermal conductivity material as the heat dissipating mass will also increase temperature sensor accuracy. Because the electrode material transmits thermal energy so rapidly, the temperature of the outer surface of the electrode will be closer to the temperature of an internal sensing point and accuracy will improve. Such is the result in a catheter design in accordance with the principles of the invention.

Figure 6:
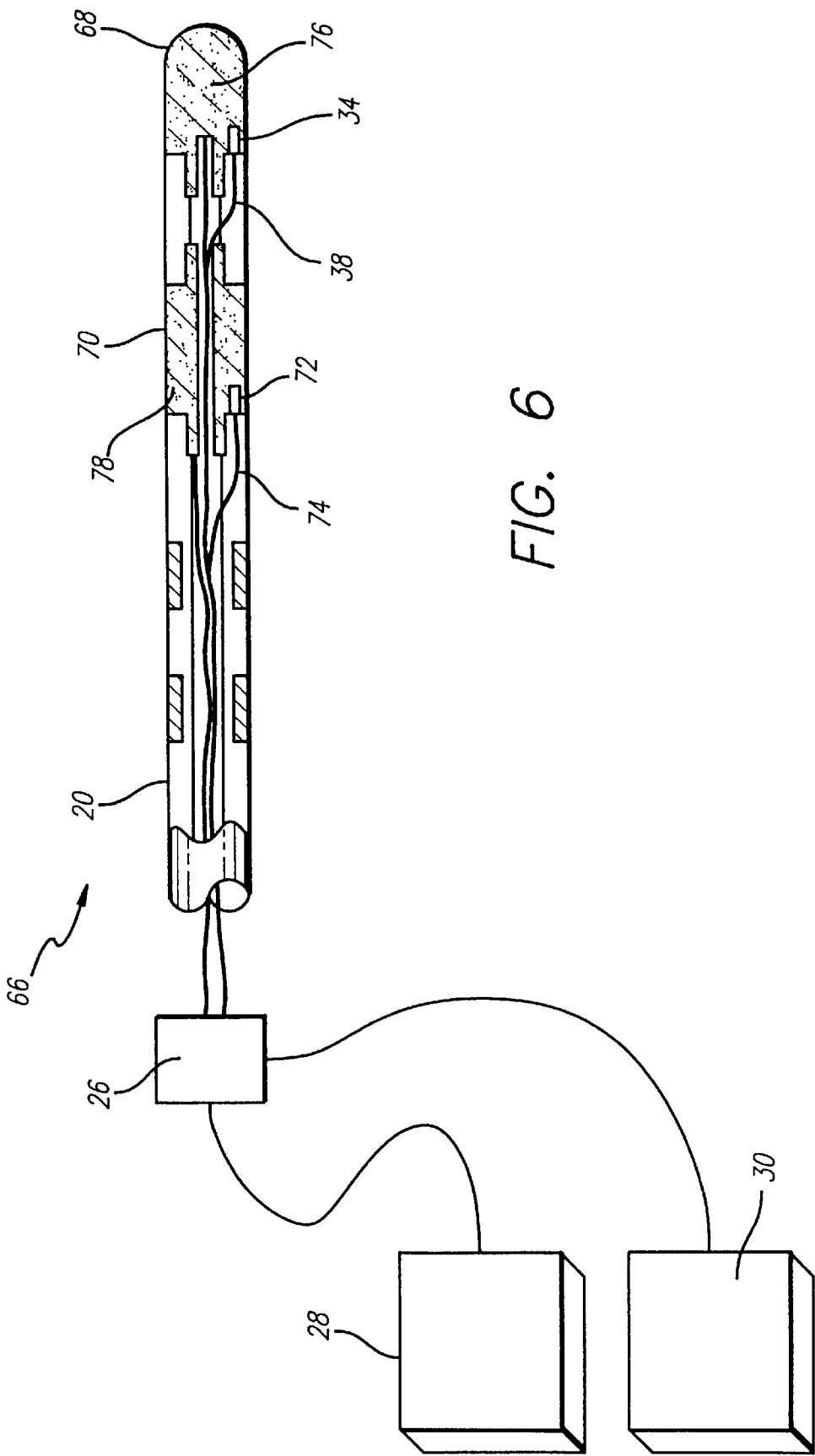
FIG. 6 presents a further embodiment in which the tip electrode and a band electrode include thermal dissipating masses and bio-compatible outer surfaces.

Referring now to FIG. 6, a catheter 66 is shown having a distal tip electrode 68 and at least one band electrode 70 mounted at its distal end proximal to the distal tip electrode. Both of these electrodes 68 and 70 include thermal dissipating masses 76 and 78 formed of high thermal conductivity material. Additionally, a temperature sensor 34 is positioned in the distal tip electrode 68 as described previously. Although the sensor wire is shown terminating at the band electrode 70, this is for clarity in the drawing. In practice, the wire would extend to the proximal end of the catheter for connection to particular equipment.

The tip electrode 68 and the band electrode 70 may be formed with outer layers of bio-compatible material in a manner shown in FIG. 4 or may be constructed entirely of a homogenous bio-compatible material in the manner shown in FIG. 5. In another arrangement, one electrode may be constructed in a manner consistent with FIG. 4 while the other is constructed consistent with FIG. 5. The two electrodes 68 and 70 may be used for bipolar ablation or may be used separately in unipolar ablation procedures. When used in a unipolar ablation procedure, the second electrode results in a back-up system in the event that the first electrode becomes unusable.

Also shown in FIG. 6 is a second temperature sensor 72 for monitoring the temperature of the band electrode 70. As in the case of the first temperature sensor 34, the wire 74 of the second temperature sensor 72 is terminated in the drawing for the purpose of retaining clarity in the figure.

Although only one band electrode 70 is shown having a thermal dissipating mass 78, additional band electrodes may likewise include such masses and additional temperature sensors. Additionally, as with the distal tip electrode, the band electrode that includes a bio-compatible outer layer and a thermal dissipation mass may also be five mm or less in length.

Therefore in accordance with the invention, there has been provided a distal tip electrode small enough to provide high resolution mapping yet large enough to provide an ablation volume comparable to much larger electrodes. Because of its small size, maneuverability is increased as is the ability to focus ablation energy better. The thermal dissipation mass permits the application of a smaller amount of ablation energy than that used with larger electrodes yet achieves a satisfactory ablation volume. It is estimated that only 8 to 50 watts of power will be needed to achieve the same ablation volume that an 8 mm electrode tip would achieve with 60 to 100 watts. In two cases, ablation volumes achieved with a catheter constructed in accordance with the invention were compared with ablation volumes achieved with larger catheters. It was found that a six French, two mm length electrode of gold alloy resulted in an ablation volume that was twice the size of that created with a six French two mm length pure platinum electrode. In the second comparison, a seven French four mm length gold alloy electrode achieved an ablation volume twice that of a seven French four mm platinum alloy electrode. The lower power requirement is also beneficial in that the patient is not exposed to larger power levels with the possibility of harm.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A catheter for mapping and ablating biological tissue, the biological tissue being located in a biological structure in which fluids flow past the tissue to be ablated, the catheter having a size such that it can be percutaneously positioned at the tissue to be ablated, the catheter comprising:

a body member having a size such that it can be percutaneously introduced to a patient and having a distal end and a proximal end;

an electrode mounted at the distal end of the body member with a distal tip extending distally from the body member, the distal tip having a size such that it can provide relatively high resolution mapping and a shape and a length such that when positioned against the tissue for ablation, a portion of the distal tip is not in contact with the tissue and extends into contact with the fluids in the biological structure for communicating heat to the fluids thereby cooling the electrode, the electrode comprising:

an outer surface formed of a biologically compatible material with a thermal conductivity at least as great as platinum 10 iridium that completely covers the distal tip; and a thermal dissipating mass formed of a material having a thermal conductivity greater than pure platinum, said mass extending into the distal tip and said portion extending into the distal tip being completely covered by the outer surface for dissipating heat received by the electrode.

2. The catheter of claim 1 wherein the outer surface of the electrode comprises a layer of bio-compatible material intimately bonded to the thermal dissipating mass, the material of the outer layer selected to have a thermal conductivity at least as great as that of platinum 10 iridium.

3. The catheter of claim 2 wherein the material of the outer layer of the electrode is selected from a bio-compatible material in the group consisting of:

gold and gold alloys;

platinum and platinum alloys;

titanium;

tungsten;

stainless steel; and cobalt based bio-compatible materials.

4. The catheter of claim 1 wherein the electrode is formed of a material having a thermal conductivity exceeding:

$$0.165 \frac{cal \times cm}{s \times °C. \times cm^2}$$

where:

C=centigrade cm=centimeters s=seconds cal=calories.

5. The catheter of claim 1 further comprising:

an electrical conductor connected to the electrode and extending to the proximal end of the body member;

wherein the electrical conductor is formed of a material having a thermal conductivity greater than platinum, and has a larger diametrical size than the size needed to conduct the amount of electricity to the electrode for ablation;

wherein the electrical conductor conducts heat away from the electrode.

6. The catheter of claim 5 wherein the electrical conductor is formed of a copper alloy.

7. The catheter of claim 1 wherein the electrode has a rounded shape and a length of not more than five mm.

8. The catheter of claim 1 further comprising a temperature sensor mounted in the thermal mass for sensing the temperature of the electrode.

9. The catheter of claim 1 further comprising a band electrode mounted at the distal end of the body member and comprising:

an outer surface formed of a biologically compatible material with a thermal conductivity at least as great as platinum 10 iridium; and a thermal dissipating mass formed of a material having a thermal conductivity greater than pure platinum and disposed in contact with the outer surface for dissipating heat received by the electrode.

10. The catheter of claim 9 wherein the outer surface of the band electrode comprises a layer of bio-compatible material intimately bonded to the thermal dissipating mass, the material of the outer layer selected to have a thermal conductivity at least as great as that of platinum 10 iridium.

11. A catheter for mapping and ablating biological tissue, the biological tissue being located in a biological structure in which fluids flow past the tissue to be ablated, the catheter having a size such that it can be percutaneously positioned at the tissue to be ablated, the catheter comprising:

a body member having a size such that it can be percutaneously introduced to a patient and having a distal end and a proximal end;

an electrode mounted at the distal end of the body member, the electrode having a size such that it can provide relatively high resolution mapping and a shape and a length such that when positioned against the tissue for ablation, a portion of the electrode is not in contact with the tissue and extends into contact with the fluids in the biological structure for communicating heat to the fluids thereby cooling the electrode, the electrode comprising:

an outer surface formed of a biologically compatible material with a thermal conductivity at least as great as platinum 10 iridium, wherein the outer surface completely covers the electrode portions to be positioned against tissue and in contact with the fluids of the biological structure; and a thermal dissipating mass formed of a material having a thermal conductivity greater than pure platinum and disposed in contact with the outer surface for dissipating heat received by the electrode;

a band electrode mounted at the distal end of the body member and comprising:

an outer surface formed of a biologically compatible material with a thermal conductivity at least as great as platinum 10 iridium; and a thermal dissipating mass formed of a material having a thermal conductivity greater than pure platinum and disposed in contact with the outer surface for dissipating heat received by the electrode;

wherein the outer surface and the thermal dissipating mass of the band electrode are formed as a unitary structure of a homogenous alloy of material having a thermal conductivity exceeding pure platinum.

12. The catheter of claim 9 further comprising a temperature sensor mounted in the thermal mass of the band electrode for sensing the temperature of the electrode.

13. The catheter of claim 1 wherein:

the electrode has a generally cylindrical shape with a rounded end so that when engaged with the tissue to be ablated, a portion of the electrode outer surface contacts the fluids in the biological structure;

the thermal mass being located in contact with the outer surface for conducting heat received from the tissue through the outer surface and to the fluids.

14. A catheter for mapping and ablating biological tissue, the biological tissue being located in a biological structure in which fluids flow past the tissue to be ablated, the catheter having a size such that it can be percutaneously positioned at the tissue to be ablated, the catheter comprising:

a body member having a size such that it can be percutaneously introduced to a patient and having a distal end and a proximal end;

an electrode mounted at the distal end of the body member and having a distal tip extending distally from the body member, the distal tip having a size such that it can provide relatively high resolution mapping and a shape and a length such that when positioned against the tissue for ablation, a portion of the electrode is not in contact with the tissue and extends into contact with the fluids in the biological structure for communicating heat to the fluids thereby cooling the electrode, the electrode comprising a thermal dissipating mass, a portion of which extends into the distal tip, said distal tip portion being formed entirely of a biologically compatible material having a thermal conductivity greater than pure platinum for dissipating heat received by the electrode.

15. The catheter of claim 14 wherein the electrode is formed entirely of a homogenous bio-compatible material selected from the group consisting of:

gold and gold alloys;

pure titanium; and pure tungsten.

16. The catheter of claim 14 further comprising:

an electrical conductor connected to the electrode and extending to the proximal end of the body member;

wherein the electrical conductor is formed of a material having a thermal conductivity greater than platinum, and has a larger diametrical size than the size needed to conduct the amount of electricity to the electrode for ablation;

wherein the electrical conductor conducts heat away from the electrode.

17. The catheter of claim 16 wherein the electrical conductor is formed of a copper alloy.

18. The catheter of claim 14 wherein the electrode has a rounded shape and a length of not more than five mm.

19. The catheter of claim 14 further comprising a temperature sensor mounted in the thermal mass for sensing the temperature of the electrode.

20. The catheter of claim 14 further comprising a band electrode mounted at a distal end of the body member and comprising:

an outer surface formed of a biologically compatible material with a thermally conductivity at least as great as platinum 10 iridium; and a thermal dissipating mass formed of a material having a thermal conductivity greater than pure platinum and disposed in contact with the outer surface for dissipating heat received by the electrode.

21. The catheter of claim 20 wherein the outer surface of the band electrode comprises a layer of bio-compatible material intimately bonded to the thermal dissipating mass, the material of the outer layer selected to have a thermal conductivity at least as great as that of platinum 10 iridium.

22. The catheter of claim 20 wherein the outer surface and the thermal dissipating mass of the band electrode are formed as a unitary structure of a homogenous alloy of material having a thermal conductivity exceeding pure platinum.

23. The catheter of claim 20 further comprising a temperature sensor mounted in the thermal mass of the band electrode for sensing the temperature of the electrode.

24. A catheter for mapping and ablating biological tissue, the biological tissue being located in a biological structure in which fluids flow past the tissue to be ablated, the catheter comprising:

a body member having a size such that it can be percutaneously introduced to a patient and having a distal end and a proximal end; and a tip electrode mounted at the distal end of the body member, the electrode having a size such that it can provide relatively high resolution mapping and a shape and a length such that when positioned against the tissue for ablation, a portion of the electrode is not in contact with the tissue and extends into contact with the fluids in the biological structure for communicating heat to the fluids thereby cooling the electrode;

wherein the tip electrode is formed of a chemically inert, biocompatible and homogeneous material having a thermal conductivity exceeding pure platinum.

25. The catheter of claim 24 wherein the material of the tip electrode is selected from the group consisting of:

gold and gold alloys;

pure titanium; and pure tungsten.

26. The catheter of claim 24 further comprising:

an electrical conductor connected to the tip electrode and extending to the proximal end of the body member;

wherein the electrical conductor is formed of a material having a thermal conductivity greater than platinum, and has a larger diametrical size than the size needed to conduct the amount of electricity to the tip electrode for ablation;

wherein the electrical conductor conducts heat away from the electrode.

27. The catheter of claim 26 wherein the electrical conductor is formed of a copper alloy.

28. The catheter of claim 24 wherein the tip electrode has a rounded shape and a length of not more than five mm.

29. The catheter of claim 24 further comprising a temperature sensor mounted on the tip electrode for sensing the temperature of the tip electrode.

30. The catheter of claim 24 further comprising a band electrode mounted at a distal end of the body member proximal from the tip electrode, said band electrode formed of a chemically inert, biocompatible and homogeneous material having a thermal conductivity exceeding pure platinum.

31. The catheter of claim 30 wherein the material of the band electrode is selected from the group consisting of:

gold and gold alloys;

pure titanium; and pure tungsten.

32. The catheter of claim 30 further comprising a temperature sensor mounted to the band electrode for sensing the temperature of the band electrode.

* * * * *

UNITED STATES PATENT AND TRADEMARK OFFICE
CERTIFICATE OF CORRECTION

PATENT NO. : 6,099,524
DATED : Aug. 8, 2000
INVENTOR(S) : David Lipson, Marc Jensen It is certified that error appears in the above-identified patent and that said Letters Patent is hereby corrected as shown below:

Column 2, lines 57,62,63 and 64 (two occurrences), remove the "." after "C".

Column 4, line 5, in the denominator of the equation, delete the ".", after "C".

Column 8, line 37, change "0.25" from bold type to normal type.

Column 12, line 34, claim 4, in the denominator of the equation, delete the "." after "C".

Signed and Sealed this

Twenty-second Day of May, 2001

Attest:

NICHOLAS P. GODICI

Attesting Officer   Acting Director of the United States Patent and Trademark Office